United States Patent [19]
Inagaki et al.

[11] Patent Number: 5,773,624
[45] Date of Patent: Jun. 30, 1998

[54] METHOD FOR PREPARING 5-AMINO-1,2,4-THIADIAZOL ACETIC ACID DERIVATIVES

[75] Inventors: Takashi Inagaki; Yasuyuki Kurita; Akihito Mizutani; Masao Kondo, all of Osaka-fu, Japan

[73] Assignee: Katayama Seiyakusyo Co., Ltd., Osaka, Japan

[21] Appl. No.: 813,199

[22] Filed: Mar. 7, 1997

[30] Foreign Application Priority Data

Mar. 15, 1996 [JP] Japan .................................. 8-059044
Nov. 12, 1996 [JP] Japan .................................. 8-300121

[51] Int. Cl.⁶ ............................................ C07D 285/08
[52] U.S. Cl. .................................................. 548/128
[58] Field of Search ........................................ 548/128

[56] References Cited

U.S. PATENT DOCUMENTS 4,107,377  8/1978  Tobin ...................................... 548/128
4,567,275  1/1986  Teraji ...................................... 548/128

FOREIGN PATENT DOCUMENTS 536900     4/1993   European Pat. Off. .
4-77477    3/1992   Japan ...................................... 548/128
2218095    11/1989  United Kingdom .

OTHER PUBLICATIONS

Wheeler, J. of Antibiotics 39 (1) 111, 1986.
Wheeler, W. J., et al, The Journal of Antibiotics, vol. XXXIX, No. 1, 111–120 (Jan. 1986).
Katritzky, A. R., et al, Comprehensive Heterocyclic Chemistry, vol. 6, Part 4B, p. 507, scheme 145, Pergamon Press, New York, 1965.

*Primary Examiner*—Robert Gerstl

[57] ABSTRACT

The invention provides useful intermediates as acylating agents for preparing 7-acylaminocephalosporin compounds which show excellent antimicrobial activities. More particularly, the present invention relates to a process for preparing 5-amino-1,2,4-thiadiazole acetic acid derivatives.

4 Claims, No Drawings

METHOD FOR PREPARING 5-AMINO-1,2,4-THIADIAZOL ACETIC ACID DERIVATIVES

FIELD OF THE INVENTION

The present invention relates to a method for preparing 5-amino-1,2,4-thiadiazole derivatives, in particular, to intermediates of 2-substituted hydroxy-imino-2-(5-amino-1,2,4-thiadiazol-3-yl) acetic acids (syn-isomer) (I) useful for acylation of 7-acylamino-cephalosporins and to a method for preparation thereof.

An object of the present invention is to provide 2-substituted-hydroxyimino-2-(5-amino-1,2,4-thiadiazol-3-yl)acetic acids (syn-isomer) of general formula (I) which are useful for acylation in preparation of 7-acylamino-cephalosporins having an strong antibiotic activity. More particularly, the present invention provides (1) a method for preparing 2-substituted hydroxy-imino-2-(5-amino-1,2,4-thiadiazol-3-yl)acetic acids (acetic esters or acetic amides) (anti-isomer) of formula (VI), and (2) a method for preparing compounds of formula (I) (syn-isomer) starting from the compound of formula (VI) (anti-isomer) via 2-substituted hydroxyimino-2-(5-formamido-1,2,4-thiadiazol-3-yl)acetic acid derivatives (acetic esters or acetic amides) (syn-isomer) of formula (VII), and (3) novel compounds having the general formula (V).

BACKGROUND OF THE INVENTION

Various processes for production of 2-substituted hydroxyimino-2-(5-amino-1,2,4-thiadiazol-3-yl)acetic acids have been reported. For example, a method for preparing 2-methoxyimino-2-(5-amino-1,2,4-thiadiazol-3-yl)acetic acid (syn-isomer) was reported which comprises forming a thiadiazole ring from ethoxycarbonyl-formamidine bromide and potassium rhodanide (KSCN) to obtain 5-amino-3-ethoxycarbonyl-1,2,4-thiadiazole, protecting an amino group and preparing the final compound through several steps (a).

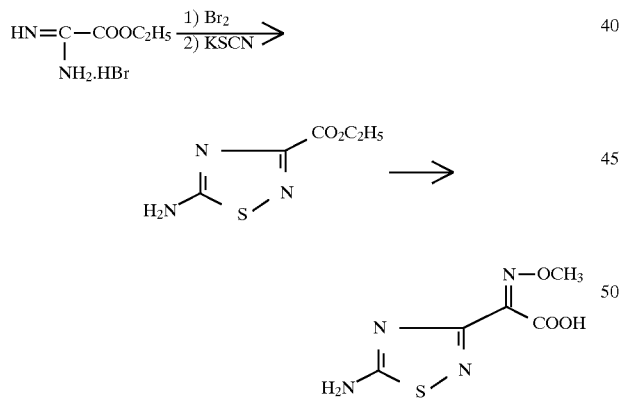

(a) J. Antibiotics 37, 557–571 (1984)

However the method comprises numerous steps and is unsuitable as an industrial process.

A method of preparing 2-substituted hydroxyimino-2-(5-amino-1,2,4-thiadiazol-3-yl)acetic acid (syn-isomer) is also known which comprises preparing a bromide of 2-cyano-2-substituted hydroxyimino-acetoamidine starting from 2-cyano-acetamide, forming a thiadiazole ring with potassium rhodanide (KSCN) to obtain 2-substituted hydroxyimino-2-(5-amino-1,2,4-thiadiazol-3-yl) acetonitrile, followed by hydrolysis to obtain 2-substituted hydroxyimino-2-(5-amino-1,2,4-thiadiazol-3-yl)acetic acids (syn-isomer) (b).

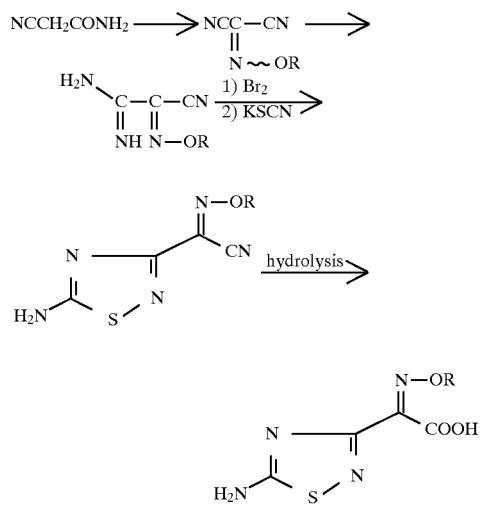

(b) Japanese Patent Publication B No. Hei 4-76990 (1992)

However, the yield of the last step of hydrolysis in the above mentioned method is low and the method is also unsuitable as an industrial process.

A method is also disclosed which comprises amidation of the nitrile obtained in the above method with hydrogen peroxide followed by hydrolysis to prepare 2-substituted hydroxyimino-2-(5-amino-1,2,4-thiadiazol-3-yl)acetic acids (c).

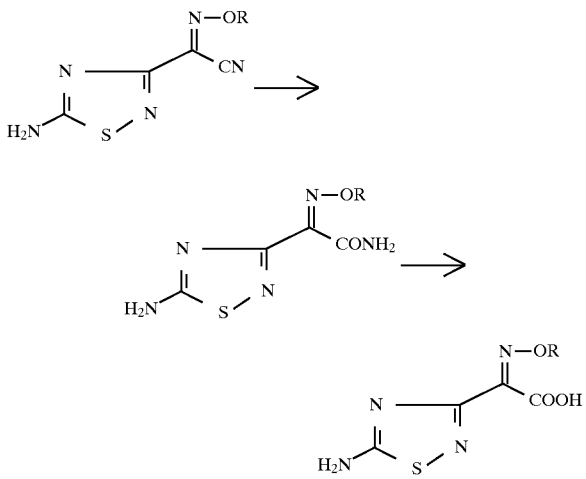

(c) Japanese Patent Publication B No. Hei 7-55941 (1995)

However, the method includes 9 steps and also requires a dangerous reagent to prepare the nitrile, and therefore, it is problematical to use as an industrial process.

A method for preparing 2-substituted hydroxyimino-2-(5-amino-1,2,4-thiadiazol-3-yl) acetic acid comprising a different cyclization reaction from those in the three methods (a), (b) and (c) is also known. In this method, 3-amino-isoxazole is reacted with MSCN and acyl halide to obtain a 5-amino-1,2,4-thiadiazol ring (d: EP0536900A).

However, one of the starting materials, 3-amino-isoxazole, cannot easily be obtained.

Therefore, development of a new method for preparing 2-substituted-hydroxyimino-2-(5-amino-1,2,4-thiadiazol-3-yl)acetic acids without such drawbacks has been desired.

SUMMARY OF THE INVENTION

As the result of an intensive study, it has now been found that 5-amino-1,2,4-thiadiazole derivatives can be produced in good yield by cyclization of O-arylsulfonyl-substituted amidoxime or O-alkylsulfonyl-substituted amidoxime with MSCN (in which M represents alkaline metal or ammonium) in a solvent.

In the first aspect of the invention, a thiadiazole ring is formed by an O-substituted compound of amidoxime (R(NH$_2$)C=NOH) and MSCN (cf. Scheme 1), and the ring formation is different from conventional methods in which a halide of amidine (RC(=NH)—NH$_2$) is reacted with KSCN (cf. (1), (2) and (3) previously mentioned).

According to the present invention using amidoxime, either syn- or anti-isomer of amidoxime can be cyclized. On the other hand, anti-isomer of amidine derivative cannot be produced in conventional methods, that is, a thiadiazol ring cannot be obtained from an anti-isomer.

The cyclization reaction of the present invention can be shown by the following Scheme 1.

Scheme 1

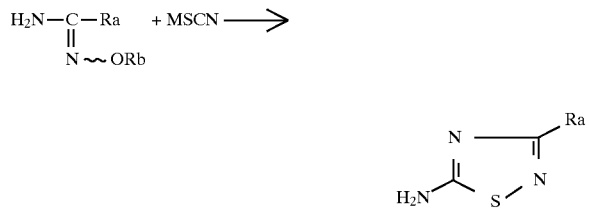

in which R$_a$ represents, for example, unsubstituted or substituted lower alkyl, or

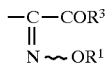

wherein R$^1$ is lower alkyl or fluoromethyl, R$^3$ is lower alkyloxy or amino, and R$_b$ represents, for example, alkylsulfonyl or arylsulfonyl, M represents, for example, alkaline metal or ammonium.

Using the cyclization reaction, the present invention provides a method for preparing 2-substituted hydroxyimino-2-( 5-amino-1,2,4-thiadiazol-3-yl)acetic acid derivatives (acetic esters or acetic amides) (anti-isomer) of formula (VI).

In the second aspect of the present invention, the present invention provides a method which comprises converting the cyclized product of formula (VI), an anti-isomer, to a syn-isomer thereof and hydrolyzing the syn-isomer in good yield.

It is known that an anti-isomer of formula (VI) can be converted to a carboxylic acid in the form of an anti-isomer by directly hydrolyzing.

Surprisingly, it has been found that the cyclized product of formula (VI) (an anti-isomer) can be converted to a syn-isomer while simultaneously also converting to a formamide derivative. The present invention is accomplished based on the above finding.

The formamide derivative of formula (VII) in the form of syn-isomer can be hydrolyzed to a syn-isomer of a carboxylic acid of formula (I) which is useful as an intermediate for 7-acylamino-cephalosporin compounds.

According to the third aspect, the present invention provides a novel compound, 2-substituted hydroxyimino-2-substituted carbonyl-acetamide-O-substituted oxime of formula (V).

Thus, more particularly, the present invention provides a method of preparing 2-substituted hydroxyimino-2-(5-amino- 1,2,4-thiadiazol-3-yl) acetic acid derivatives (anti-isomer) of the general formula (VI):

wherein R$^1$ is lower alkyl or fluoromethyl, R$^3$ is lower alkyloxy or amino, which comprises reacting of 2-substituted hydroxyimino-2-substituted carbonyl-acetamide-O-substituted oxime of the general formula (V):

wherein R$^1$ and R$^3$ have the same meanings as above and R$^2$ is alkylsulfonyl or arylsulfonyl, with MSCN wherein M is alkaline metal or ammonium.

The present invention also provides a method of preparing 2-substituted hydroxyimino-2-(5-formamido-1,2,4-thiadiazol-3-yl) acetic acid derivatives (syn-isomer) of the general formula (VII):

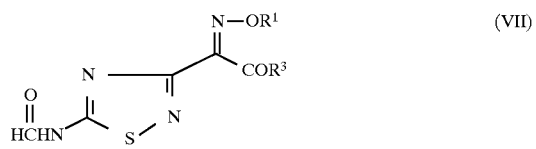

wherein R$^1$ is lower alkyl or fluoromethyl, R$^3$ is lower alkyloxy or amino, which comprises reacting formic acid with 2-substituted hydroxyimino-2-(5-amino-1,2,4-thiadiazol-3-yl)acetic acid derivatives (anti-isomer) of the general formula (VI):

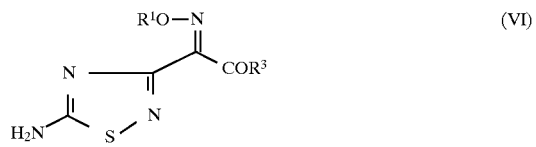

wherein R$^1$ and R$^3$ have the same meanings as above. The resulting syn-isomer is hydrolyzed to give the desired intermediate, 2-substituted hydroxyimino-2-(5-amino-1,2,4-thiadiazol-3-yl) acetic acid (syn-isomer) of the formula (I):

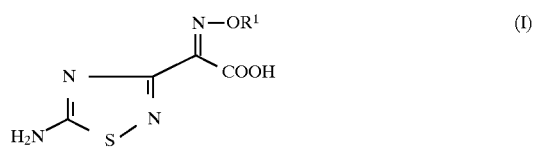

wherein R$^1$ is lower alkyl, fluoromethyl. The intermediate is used for the acylation of 7-acylcephalosporin compounds.

In addition, the compound of the formula (V) is a novel compound and therefore, the invention provides 2-substituted hydroxyimino-2-substituted carbonyl-acetamide-O-substituted oxime of the general formula (V):

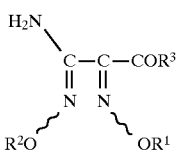
(V)

wherein $R^1$ represents methyl, ethyl or fluoromethyl, $R^2$ represents methanesulfonyl, benzenesulfonyl or toluenesulfonyl and $R^3$ represents lower alkyloxy or amino, provided that when $R^1$ represents methyl, $R^3$ does not represent ethoxy.

DETAILED DESCRIPTION OF THE INVENTION

As used herein, the term "lower alkyl" represents a residue of a saturated straight or branched hydrocarbon having 1 to 6 carbon atoms, preferably 1 to 5, most preferably 1 to 4 of carbon atoms. Typical lower alkyl groups include methyl, ethyl, n-propyl, isopropyl, butyl, t-butyl and the like.

"Arylsulfonyl" or "alkylsulfonyl" represents a sulfonyl group which can be conventionally used as a protecting group for a oxime group, for example, benzenesulfonyl, toluenesulfonyl, methanesulfonyl and the like.

Suitable examples of alkaline metals M of "MSCN" include sodium, potassium and the like.

According to the present invention, 2-substituted hydroxyimino-2-(5-amino-1,2,4-thiadiazol-3-yl) acetic acid (syn-isomer) of formula (I), which is useful for acylation for preparing 7-acylamino-cephalosporin compounds, may be prepared in 6 or 7 steps which are summarized by the following scheme 2, starting from cyanoacetic esters.

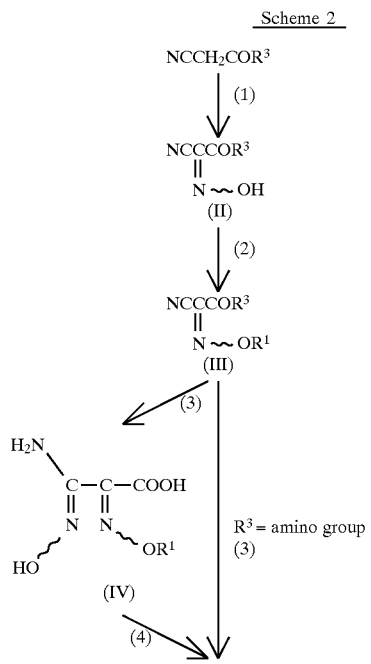

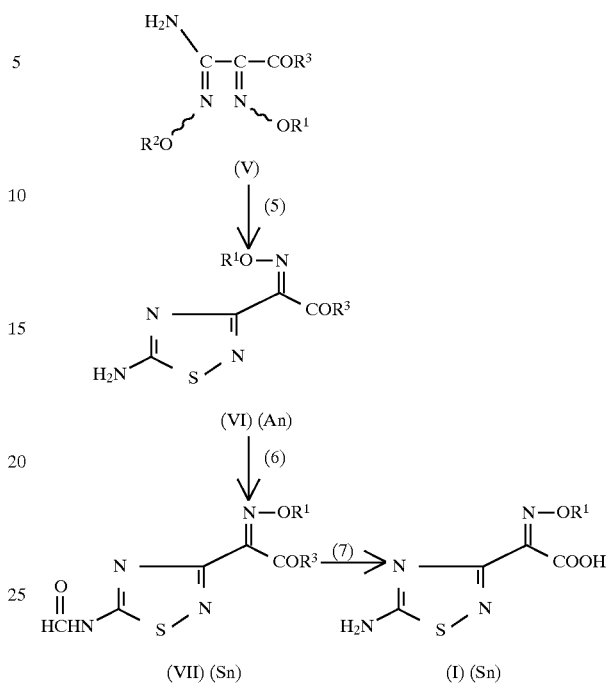

In scheme 2, a compound of formula (VI) of the present invention obtained by reaction of a compound (V) with MSCN is an anti-isomer. The anti-isomer compound of formula (VI) may be isomerized by formic acid to the syn-isomer and simultaneously the amino group undergoes formylation.

In the intermediates of formula (II), (III), (IV) and (V), the stereochemistry of the moiety having the formula:

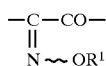

may include both stereoisomers having the following formula (sn) and (An):

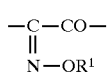 (Sn)

 (An)

wherein $R^1$ has the same meaning as above mentioned.

As used herein, for all compounds having the above moiety, a compound having the formula (Sn) may be referred to as "syn-isomer" and a compound having the formula (An) may be referred to as "anti-isomer".

The advantages in the reactions of the invention can be shown as follows:

(1) The final compounds can be obtained by a short step process in good yield starting from the inexpensive cyanoacetic ester.

(2) Compared to conventional methods, the method of the invention via the compound of formula (V) can be safely performed and advantageously used for industrial production because it does not require any expensive or dangerous reagents.

(3) In a conventional method for preparing a syn-isomer of the compound of formula (I) by direct hydrolysis of the compound (VI) (syn-isomer), by-products are formed and the yield of the compound of formula (I) decreased. According to the method of the invention, compound (I) of high purity can be obtained in a high yield by hydrolysis of the compound (VII) which corresponds to the compound (VI) of which the amino group ($NH_2$) is protected by a formyl group. Therefore, the method of the invention preparing the compound of formula (VII) by a one step reaction from the compound (VI) is eminently suitable for industrial production. For example, compound of formula (VII) wherein $R^1$ is methyl can be quantitatively obtained from compounds of formula (VI).

The method of preparing the desired intermediate of formula (I) is illustrated in accordance with the steps in Scheme 2 as follows.

Step (1)

A compound of formula (II) in which $R^3$ is amino may be prepared by converting a cyanoacetic ester with aqueous ammonia to an amide, which is subjected to nitroso reaction to give the compound of formula (II). A compound of formula (II) in which $R^3$ is lower alkyloxy may be prepared by subjecting a cyanoacetic ester to a nitroso reaction. Nitroso reagent used in the reaction are those which are conventionally used for forming a C-nitroso product by reacting with an active methylene, for example, sodium nitrite and the like.

Step (2)

A compound of formula (III) may be prepared by the reaction in which a substituent is introduced to a hydroxy-imino group of a compound of formula (II). Reagents for introducing a substituent into a hydroxyimino group of a compound of formula (II) include compounds of formula $R^1$-Y in which $R^1$ has the same meaning as above and Y represents a halogen atom. Suitable acid residues are —Cl, —Br and —I, and a residue of alkyl sulfate such as methyl sulfate, ethyl sulfate and the like.

The reaction can be performed in water or in a solvent such as dimethyl formamide, dimethyl sulfoxide, acetonitrile and the like, or other solvents which do not negatively affect the reaction. The reaction can be accomplished in the presence of an organic or an inorganic base. The reaction may be accomplished at any temperature, however, generally under heating.

Step (3)

When a compound of formula (III) in which $R^3$ is lower alkyloxy is used as a starting material, the step involves a hydrolysis followed by amidoxime reaction. The hydrolysis may be conveniently performed in the presence of a base. Examples of a suitable base are alkaline metal (for example, sodium, potassium and the like) hydroxides, carbonates and hydrogencarbonates or alkaline earth metal (for example, magnesium, calcium and the like) hydroxides, carbonates or hydrogencarbonates. The reaction can be accomplished in water or alcohol, or a mixture thereof. The reaction temperature may be below 10° C., preferably from 0° to 5° C. The product formed by hydrolysis is converted to an amidoxime.

The compound of formula (III) in which $R^3$ is amino can be directly converted to amidoxime, or alternatively it can be subjected to hydrolysis at the same time as the amidoxime reaction.

The amidoxime reaction is conveniently performed by reaction with hydroxylamine hydrochloride or sulfate in the presence of a base. Suitable bases include an alkaline metal carbonate, hydrogencarbonate and the like. The reaction can be performed in water or alcohol, or a mixture thereof. The reaction temperature may be 20° to 80° C.

Step (4)

In a conventional method, a compound of formula (V) has been prepared by direct amidoxime reaction of a compound of formula (III) in which $R^3$ is ethoxy, followed by reaction with p-toluenesulfonyl chloride ((5) J. Antibiotics, 39, 111–121 (1986)). It is impossible to carry out this method on a large scale due to a poor yield. Therefore, the inventor of the invention employed a route via compounds of formula (III)→(IV)→(V). A compound of formula (III) in which $R^3$ is amino group can be directly converted to an amidoxime and then to an aryl sulfonyl product or an alkyl sulfonyl product of formula (V).

Alternatively, a compound of formula (V) can be obtained by converting to a lower alkyl ester and then to an aryl sulfonyl product or an alkyl sulfonyl product of formula (V).

A lower alkyl ester of formula (IV) can be obtained by a conventional method for preparing a lower alkyl ester.

A suitable example of such methods for industrial production includes a method using a lower alcohol and an acid catalyst such as hydrochloric acid. The reaction temperature is in the range from 20° C. to 65° C.

After the reaction of preparing an aryl sulfonyl or an alkyl sulfonyl product, without purification, the reaction mixture may be concentrated by evaporating alcohol followed by reacting with an aryl sulfonyl chloride or an alkyl sulfonyl chloride to give a compound of formula (V).

The reaction can be performed in a solvent such as ethyl acetate, methanol, acetonitrile and the like, or other solvents which do not negatively affect the reaction. The reaction can be accomplished in the presence of organic or inorganic bases. The reaction temperature is below 10° C. and is preferably 0°±2° C.

Step (5)

A compound of formula (VI) can be prepared by reaction of a compound of formula (V) with MSCN in which M represents alkaline metal or ammonium. Suitable alkaline metals include sodium, potassium and the like. The reaction can be performed in a solvent such as methanol, acetone, acetonitrile and the like, or in a solvent which does not negatively affect the reaction. The volume of solvent used may be 2 to 10 times, preferably 3 to 4 times the volume of the compound of formula (V). The amount of MSCN may be 1.5 to 5 equivalents, preferably 3 to 4 equivalents based on the amount of the compound of formula (V). The reaction temperature is 0° to 60° C. and is preferably 20° to 40° C.

Step (6)

A compound of formula (VII) may be prepared by reaction of a compound of formula (VI) with formic acid or formic acid and acetic anhydride. Formic acid may be used 2 to 10 times by weight, preferably 3 to 5 times based on the compound of formula (VI) and it may be of a purity of more than 98% and also can be in chemical grade. The reaction temperature is 30° to 80° C. and it is preferably 50° to 70° C. For example, since the compound of formula (VII) is precipitated as the reaction proceeds, and therefore, equilibration of the reaction can be moved and the compound of formula (VII) is predominantly produced.

Step (7)

A compound of formula (I) can be prepared by hydrolysis of a compound of formula (VII). The hydrolysis may be performed in the presence of a base. Examples of a suitable base are hydroxides of an alkaline metal such as sodium, potassium, lithium and the like, an alkaline earth metal such as magnesium, calcium and the like, preferably sodium hydroxide.

The reaction can be performed in a aqueous solvent such as water, a mixture of alcohol and water. The reaction temperature of hydrolysis is 0° to 10° C. and it is preferably 0° to 5° C., further may be raised to 40° to 60° C. under heating.

The following examples are illustrative only and are not intended to limit the scope of the invention.

EXAMPLES

Reference Example 1

Preparation of 5-amino-3-methyl-1,2,4-thiadiazole

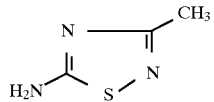

(1) Preparation of acetamide oxime

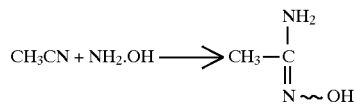

A solution of acetonitrile (12.4 g, 0.30 mol), hydroxylamine hydrochloride (27.2 g, 0.39 mol), sodium hydroxide (16.3 g, 0.39 mol) and water (150 ml) was stirred at room temperature for 17.5 hrs. Acetonitrile and water were distilled off under reduced pressure to dryness, and then, methanol was added to the resultant residue, and the methanol-insoluble substance (NaCl) was removed from the mixture. Then, methanol was distilled off to give acetamide oxime (13.7 g).

Yield: 61.2% m.p.: 114°–130° C.

IR(cm$^{-1}$): 3490.9, 3371.3, 3157.3, 1654.8, 1585.4, 1398.3, 893

NMR(DMSO-d$_6$)δ: 1.63(s, 3H), 5.27(bs, 2H), 7.64(bs, 1H)

(2) Preparation of acetamide-oxime tosylate

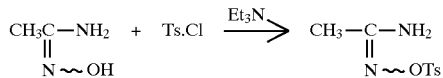

Triethylamine (3 ml, 2.18 g, 0.022 mol) was added to acetamide oxime (1.5 g, 0.02 mol) in tetrahydrofuran (THF) (45 ml). To the mixture, p-toluenesulfonyl chloride (Tosylchloride, TsCl) (4.2 g, 0.022 mol) was added in small portions (generating heat intensively). The mixture was allowed to react at room temperature for 45 mins. and the precipitates were collected by filtration. THF was distilled off under reduced pressure, and water was added to the resultant residue. The residue was extracted with ethyl acetate, and the organic layer was washed with water and dried over sodium sulfate. The ethyl acetate was distilled off under reduced pressure, and isopropyl ether was added to the residue to separate crystals. The crystals were filtered off is and dried to give acetamide-oxime-tosylate (3.2 g, yield; 69.2%).

m.p.: 88°–90° C. (decomp.)

IR(cm$^{-1}$): 3463.9, 3367.5, 1652.5, 1336.6, 1174.6, 808.1

NMR(CDCl$_3$)δ: 1.78(s, 3H), 2.39(s, 3H), 4.93(bs, 2H), 7.07–7.97(m, 4H)

(3) Preparation of 5-amino-3-methyl-1,2,4-thiadiazole

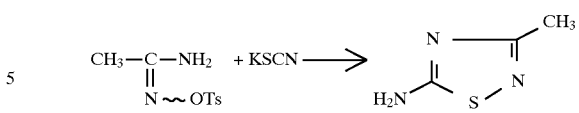

Acetamide-oxime-tosylate (2.29 g, 0.01 mol) and potassium rhodanide (1.07 g, 0.011 mol) ware dissolved in methanol (23 g) to react at 45° to 50° C. for 20 hrs. The reaction mixture was cooled to separate crystals (salt of potassium p-toluenesulfonate). The crystals were filtered off and the filtrate was concentrated. Ethyl acetate was added to the resulting residue to remove the insoluble substance. Then, the organic layer was concentrated, and the resulting residue was purified by silica gel chromatography to give 5-amino-3-methyl-1,2,4-thiadiazole (450 mg, yield: 39.1%).

m.p.: 192.5°–193.0° C.

IR(cm$^{-1}$): 3278.8, 3095.5, 1651.0, 1544.9, 1492.8, 1382.9, 810.0

NMR(DMSO-d$_6$)δ: 2.21(s, 3H), 7.59(bs, 2H)

Reference Example 2

Preparation of 1,1-dimethoxy-2-(5-amino-1,2,4-thiadiazole-3-yl)-ethane

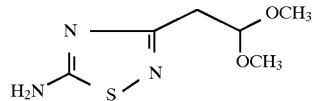

(1) Preparation of 3,3-dimethoxy-propane-amido-oxime

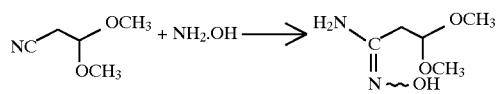

Hydroxylamine hydrochloride (41.7 g, 0.6 mol) was dissolved in water (400 ml), and 30% sodium hydroxide (115 ml) was added thereto. To the resultant mixture, 3,3-dimethoxypropanenitrile (57.5 g, 0.5 mol) and methanol (100 g) were added. The mixture was allowed to react at 40° to 43° C. overnight. After completion of the reaction, concentrated hydrochloric acid (6 g) was added to adjust the solution to pH 5 to 6. Ethanol was then distilled off under reduced pressure. The residue was extracted with ethyl acetate (300 ml) three times and the combined extracts were dried over sodium sulfate and concentrated under reduced pressure to give 3,3-dimethoxypropane-amido-oxime (53.5 g, yield: 72.3%).

b.p.: 132°–134° C./1 mmHg

IR(cm$^{-1}$): 3473.6, 3361.0, 1666.4, 1658.7, 1386.7, 1120.6, 1070.4

NMR(CDCl$_3$)δ: 2.40(w, 2H), 3.33(s, 6H), 4.43(t, 1H), 4.86(bs, 2H), 8.45(bs, 1H)

(2) Preparation of 3,3-dimethoxypropane-amido-oxime tosylate

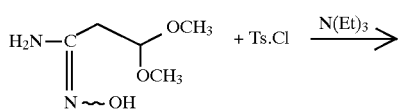

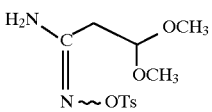

3,3-dimethoxypropane-amido-oxime (50 g, 0.34 mol) and triethylamine (37.6 g, 0.37 mol) in methylene chloride (100 ml) were added dropwise to tosyl chloride (64.6 g, 0.34 mol) in methylene chloride (200 ml) below 10° C. After completion of the reaction, the reaction mixture was washed with water, and methylene chloride and concentrated. To the resulting residue, isopropyl ether was added, and the precipitates were filtered off and dried to give 3,3-dimethoxypropane-amido-oxime tosylate (87.0 g, yield: 85.3%).

m.p.: 90.5°–92.0° C.

IR($cm^{-1}$): 3384.8, 1633.6, 1352.0, 1180.4

NMR($CDCl_3$)δ: 2.37(d, 2H), 2.41(s, 3H), 3.28(s, 6H), 4.38(t, 1H), 5.22(bs, 2H), 7.2–7.78(n, 4H)

(3) Preparation of 1,1-dimethoxy-2-(5-amino-1,2,4-thiadiazole-3-yl)-ethane

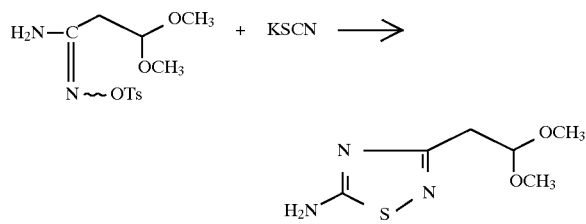

3,3-dimethoxypropane-amido-oxime tosylate (5 g, 16.5 mol) was reacted with potassium rhodanide (7.15 g, 73.6 mmol) in methanol (50 g) at 55° to 60° C. for 16 hrs. The reaction mixture was cooled to separate crystals, which were filtered off. The filtrate was concentrated under reduced pressure. Water was added to the resulting residue, and the residue was extracted with ethyl acetate (30 ml×3). The extract was purified by silica gel chromatography to give 1,1-dimethoxy-2-(5-amino-1,2,4-thiadiazole-3-yl)-ethane (1.1 g, yield: 35%).

m.p.: 62.0°–66.5° C.

IR($cm^{-1}$): 3388.7, 3130.3, 1647.1, 1539.1, 1363.6, 1114.8, 920.0

NMR(DMSO-$d_6$)δ: 2.98(d, 2H), 3.36(s, 6H), 4.84(t, 1H), 6.53(bs, 2H)

The present invention is illustrated in more detail by Preparation examples and Examples.

Preparation Example 1

Preparation of ethyl 2-hydroxyiminocyanoacetate of the formula II (wherein $R^3$ is OEt)

62.5% sulfuric acid (603.7 g) were added dropwise to sodium nitrite (507.2 g) and ethyl cyanoacetate (791.0 g) in water (2,540 ml) at 30° to 40° C. over 2.2 hrs. under cooling. After completion of the addition, the mixture was stirred at a room temperature for 2 hrs, and the nitrogen oxide ($NO_2$) was removed under reduced pressure, and the residue was cooled to 15° C. to separate crystals, which were filtered off and washed twice with water (150 ml) and twice with toluene (200 ml), and dried at 50° C. to give ethyl 2-hydroxyiminocyanoacetate (932.9 g, yield: 93.9%).

m.p.: 132°–133° C.

IR($cm^{-1}$): 3100, 3120.4, 1728.1, 1483.0, 1313.4, 1066.6, 852.5

NMR($CDCl_3$)δ: 1.29(3H, t, J=7 Hz), 4.25(2H, q, J=7 Hz), 12–15(1H, bs)

Preparation Example 2

Preparation of ethyl 2-methoxyiminocyanoacetate of the formula III (wherein $R^1$ is $CH_3$ and $R^3$ is OEt)

62.5% sulfuric acid (122.3 g, 4.32 mol) was added dropwise to an aqueous solution (2,170 ml) of ethyl cyanoacetate (678 g, 6.0 mol) and sodium nitrite (434.7 g, 6.3 mol) at an internal temperature of 24° to 30° C. over about 20 mins. The mixture was stirred at the same temperature for another 2 hrs. Potassium carbonate (129.2 g, 0.93 mol) in water (258 ml) was added dropwise over about 30 mins. to dissolve the reaction mixture. Dimethyl sulfate (756.0 g, 6.0 mol) was then added dropwise at an internal temperature of 22° to 32° C. over about 45 mins. under ice-cooling, and the mixture was stirred at a room temperature for 2 hrs.

The reaction mixture was heated at 50° C. for 1 hr. and cooled to 25° C., then potassium carbonate (7.2 g) in water (14 ml) was added to neutralize (pH 6.5 to 7.0). The reaction mixture was extracted twice with ethyl acetate (900 ml), and the extract was washed twice with saturated brine (450 ml). The ethyl acetate layer was concentrated to give a residue (797 g).

The concentrate was distilled under reduced pressure to give ethyl 2-methoxyimino-cyanoacetate as a fraction obtained under conditions of 80° to 83° C. and 2 mmHg (384.8 g, yield: 41.1%).

IR($cm^{-1}$): 1751.2, 1558.4, 1298.0, 1056.9, 840.9

NMR(δ): 1.38(t, 3H), 2.27(s, 3H), 2.35(q, 2H)

Preparation Example 3

Preparation of ethyl 2-fluoromethoxyimino-cyanoacetate of the formula III (wherein $R^1$ is $CH_2F$ and $R^3$ is OEt)

Potassium carbonate (110.6 g, 0.8 ml) was added to ethyl 2-hydroxyimino-cyanoacetate (56.8 g, 0.4 mol) in dimethylsulfoxide (200 ml) under ice-cooling, and the mixture was stirred for 10 mins, and then Fluoromethyl bromide (48.8 g, 0.4 mol) in N,N-dimethylformamide (40 ml) was added dropwise to the mixture under ice-cooling. The mixture was stirred at an internal temperature of 20° to 30° C. for 2.5 hrs. The reaction solution was dispersed in ice water (1 L), and it was extracted with ethyl acetate (800 ml, 500 ml, and 500 ml). The combined extracts were washed twice with saturated brine (300 ml) and dried over sodium sulfate, and then concentrated to give a concentrate (66.4 g) which was purified by column chromatography using silica gel (60 g) to give ethyl 2-fluoromethoxyimino-cyanoacetate (46.6 g, yield: 66.9%) as an oily substance.

IR($cm^{-1}$ KBr): 2991, 2349, 1761, 1740, 1582, 1470, 1377, 1333, 1302, 1184, 1136, 1067, 1009, 949, 860, 839, 770

NMR($CDCl_3$)δ: 1.38(3H, t, J=7 Hz), 4.38(2H, q, J=7 Hz), 5.80(2H, d, J=52 Hz)

Preparation Example 4

Preparation of 2-cyano-2-methoxyimino-acetamide of the formula III (wherein $R^1$ is Me and $R^3$ is $NH_2$)

To a solution of an aqueous concentrated ammonia (64.5 g, 1.07 mol) in water (28.7 ml), ethyl cyanoacetate (100 g, 0.89 mol) was added dropwise at −5° C. under ice-cooling.

After completion of the reaction, the mixture was concentrated under reduced pressure. A solution of sodium nitrite (73.3 g, 1.06 mol) in water (151 g) was added to the residue. The mixture was maintained at an internal temperature of 38° to 48° C., to which 62.5% sulfuric acid (76.3 g, 0.49 mol) was added dropwise. After completion of the addition, the mixture was stirred at the same temperature for 1 hr, and then potassium carbonate (73.3 g, 0.53 mol) in water (110 g) was added dropwise followed by dimethyl sulfate (133.8 g, 1.06 mol) at 38° to 48° C. The mixture was stirred at the same temperature for 1 hr. and cooled. The resulting crystals were washed with water (150 ml) at 50° C., filtered and dried to give 2-cyano-2-methoxyimino-acetamide (92.2 g, yield: 82%).

m.p.: 124°–126° C.

IR(KBr)cm$^{-1}$: 3400, 3300, 3180, 1705, 1560, 1160, 1045

NMR(DMSO-d$_6$)δ: 1.37(3H, t, J=8 Hz), 4.53(2H, q, J=8 Hz), 7.93(2H, s)

Preparation Example 5

Preparation of 2-carboxyl-2-methoxyimino-acetamidoxime of the formula IV (wherein R$^1$ is Me)

To a suspension of 2-cyano-2-methoxyimino-acetamide (24.4 g, 0.19 mol) and sodium bicarbonate (32.2 g, 0.38 mol) in water, hydroxylamine hydrochloride (13.3 g, 0.19 mol) in water (18.4 g) was added dropwise at 80° to 85° C. The mixture was stirred at the same temperature for 3 hrs. Then, the reaction solution was concentrated followed by adjusting to pH 2.0 with concentrated hydrochloric acid and then cooling to separate crystals. The crystals were filtered off, washed with methanol (20 g) and dried to give 2-carboxy-2-methoxyimino-acetamidoxime (27.1 g). The crystal contained 14.8% of sodium chloride. Practical yield: 27.1× 0.852=23.1 g. Yield: 74.8%.

m.p.: 155°–156° C. (decomp.)

IR(KBr)cm$^{-1}$: 3382, 3175, 1681.8, 1616.2, 1380.2, 1053.1, 1083.8

Preparation Example 6

Preparation of 2-carboxy-2-methoxyimino-acetamidoxime of the formula IV (wherein R$^1$ is Me)

A solution of 96% potassium hydroxide (60.9 g, 1.04 mol) in water (121 ml) was added dropwise to ethyl 2-methoxyimino-cyanoacetate (158.0 g, 1.01 mol) in water (236 ml) at 50° to 55° C., and potassium carbonate (90.9 g, 0.66 mol) and water (182 ml) were added thereto. Hydroxylamine hydrochloride (91.5 g, 1.31 mol) in water (137 ml) was added dropwise at the same temperature over about 2 hrs., and the mixture was left to stand at a room temperature overnight. The reaction solution was concentrated, to which concentrated hydrochloric acid (110.9 g, 1.06 mol) was added to adjust the pH to 1.0. The mixture was cooled to separate crystals which were filtered off, washed with water (30 ml×2) and acetone (124 ml) and dried to give 2-carboxyl-2-methoxyimino-acetamidoxime (194.0 g). This compound contained 35.5% of potassium chloride. Practical yield: 76.7%.

Preparation Example 7

Preparation of 2-carboxy-2-fluoromethoxyimino-acetamidoxime of the formula IV (wherein R$^1$ is CH$_2$F)

Sodium hydroxide (12.9 g, 321.1 mmol) in water (268 ml) was added to ethyl 2-fluoromethoxyimino-cyanoacetate (46.6 g, 267.6 mmol) under ice-cooling, and the mixture was stirred at room temperature for 3 hrs. To the reaction mixture, hydroxylamine hydrochloride (20.5 g, 294.4 mmol) and then potassium carbonate (16.7 g, 120.4 mmol) were added under ice-cooling, and the mixture was stirred at a room temperature overnight and then concentrated hydrochloric acid (22.3 ml, 267.6 mmol) was added (pH 2). The mixture was concentrated at an internal temperature of 30° C., and then cooled when crystals were separated. The crystals were filtered off and dried to give 2-carboxy-2-fluoromethoxyimino-acetamidoxime (21.3 g, yield: 44.6%).

m.p.: 103°–105° C. (decomp.)

IR(KBr)cm$^{-1}$: 3435, 3109, 2509, 1690, 1641, 1605, 1522, 1393, 1142, 1072, 802

Preparation Example 8

Preparation of O-tosyl-2-methoxycarbonyl-2-methoxyimino-acetamidoxime of the formula V (wherein R$^1$ is Me, R$^2$ is tosyl, and R$^3$ is OMe)

Thionyl chloride (124.8 g, 1.05 mol) was added dropwise to a suspension of 2-carboxy-2-methoxyimino-acetamidoxime (202 g including 20.4 g of sodium chloride, i.e., 161 g (1.0 mol) as the substance) in methanol (315 g) under reflux with heating (63° to 67° C.). After completion of the addition, it was kept under reflux for 2 hrs. and then concentrated under reduced pressure to give a residue to which ethyl acetate (260 g) was added and the resultant mixture was further concentrated. To the residual liquid, ethyl acetate (800 g), sodium bicarbonate (250 g, 3.0 mol) and p-toluenesulfonyl chloride (200 g, 1.05 mol) were added. Water (450 g) was added dropwise thereto at an internal temperature of 5° C., and the resultant mixture were stirred at the same temperature overnight. A 90% acetic acid (66.6 g, 1.0 mol) was added dropwise to neutralize the mixture, and the resultant mixture was concentrated at an internal temperature of 60° C. or lower under reduced pressure. To residual liquid, water (450 g) was added, and the mixture was cooled to separate crystals. The crystals were filtered off, washed with toluene (700 g) and dried to give O-tosyl-2-methoxycarbonyl-2-methoxyimino-acetamidoxime (263 g, yield: 79.9%).

m.p.: 122°–124° C.

IR(KBr)cm$^{-1}$: 3462, 3352, 1735.8, 1651, 1595, 1367.4, 1292.2, 1178.4, 1047.3

NMR(DMSO-d$_6$)δ: 2.10(s, 3H), 3.75(s, 3H), 4.0(s, 3H), 5.42(bs, 2H), 7.25–7.44(m, 3H)

Preparation Example 9

Preparation of O-benzenesulfonyl-2-methoxycarbonyl-2-methoxyimino-acetamidoxime of the formula V (wherein R$^1$ is Me, R$^2$ is benzenesulfonyl, and R$^3$ is OMe)

O-benzenesulfonyl-2-methoxycarbonyl-2-methoxyimino-acetamidoxime (49.6 g, yield: 77.4%) was obtained in the same procedure as described in Preparation example 8, using 2-carboxy-2-methoxyimino-acetamidoxime (41 g including 20.3% of sodium chloride, i.e., 32.7 g (0.20 mol) as the substance) and benzenesulfonyl chloride (37.8 g, 0.21 mol).

m.p.: 138°–139° C.

IR(KBr)cm$^{-1}$: 3452, 3346, 1728, 1649, 1311, 1190, 1047, 804

NMR(DMSO-d$_6$)δ: 3.65(s, 3H), 3.87(s, 3H), 7.07(bs, 2H), 7.75–7.93(m, 5H)

Preparation Example 10

Preparation of O-mesyl-2-methoxycarbonyl-2-methoxyimino-acetamidoxime of the formula V (wherein $R^1$ is Me, $R^2$ is mesyl, and $R^3$ is OMe)

There was suspended in ethyl acetate (20 ml) 2-methoxycarbonyl-2-methoxyimino-acetamidoxime hydrochloride (2.2 g, 0.01 mol) obtained in the same procedure as described in Preparation example 8, using 2-carboxy-2-methoxyimino-acetamidoxime, methanol and thionyl chloride. To the suspension, triethylamine (2.9 ml, 2.10 g, 0.02 mol) was added, and then, methanesulfonyl chloride (0.89 ml, 1.31 g, 0.011 mol) was added dropwise under ice-cooling. The resultant mixture was stirred at 5° C. for 30 mins. and then stirred at a room temperature for 1.5 hrs. The reaction mixture was washed with water, and the ethyl acetate layer was dried over sodium sulfate and concentrated. To the resulting residue, isopropyl ether was added to separate crystals which were filtered off and dried to give O-mesyl-3-methoxycarbonyl-2-methoxyimino-acetamidoxime (1.1 g, yield: 41.8%).

m.p.: 109°–112.0° C.

IR(KBr)cm$^{-1}$: 3435, 1732, 1349, 1174, 1045,

NMR(DMSO-d$_6$)δ: 3.05(s, 3H), 3.75(s, 3H), 4.00(s, 3H), 7.15(bs, 2H)

Preparation Example 11

Preparation of O-tosyl-2-methoxycarbonyl-2-fluoromethoxyimino-acetamidoxime of the formula v (wherein $R^1$ is CH$_2$F, $R^2$ is tosyl, and $R^3$ is OMe)

2-Carboxy-2-fluoromethoxyimino-acetamidoxime (1.79 g, 10 mmol) was suspended in methanol (5 ml), and thionyl chloride (1.31 g, 11 mmol) was added thereto. The mixture was heated to reflux for 4 hrs., and the methanol was distilled off to give a residue, to which ethyl acetate (5 ml) was added and the mixture was concentrated. To a suspension of the residue in ethyl acetate (9 ml), sodium bicarbonate (2.52 g, 30 mmol) and p-toluenesulfonyl chloride (1.91 g, 10 mmol) were added. Water (4.51 ml) was further added, and the mixture was stirred at 5° C. or lower for 17 hrs. The reaction mixture was treated in the same procedure as described in Preparation example 8 to give O-tosyl-2-methoxycarbonyl-2-fluoromethoxyimino-acetamidoxime (2.40 g, yield: 69.1%).

m.p.: 136°–138° C.

IR(KBr)cm$^{-1}$: 3504, 3389, 1749, 1659, 1595, 1367, 1290, 1194, 1178, 1123, 1057, 1011, 905, 795, 683

NMR(DMSO-d$_6$)δ: 2.39(3H, s), 3.69(3H, s), 5.63(2H, d, J=53 Hz), 7.18(2H, s), 7.29(2H, d, J=9 Hz), 7.69(2H, d, J=9 Hz)

Preparation Example 12

Preparation of O-benzenesulfonyl-2-methoxycarbonyl-2-fluoromethoxyimino-acetamidoxime of the formula V (wherein $R^1$ is CH$_2$F, $R^2$ is benzenesulfonyl, and $R^3$ is OMe)

2-Carboxy-2-fluoromethoxyimino-acetamidoxime (3.58 g, 20 mmol) was reacted with benzenesulfonyl chloride (3.53 g, 20 mmol) in the same procedure as described in Preparation example 11 to give O-benzenesulfonyl-2-methoxycarbonyl-2-fluoromethoxyimino-acetamidoxime (4.17 g, yield: 62.6%).

m.p.: 126°–128° C.

IR(KBr)cm$^{-1}$: 3464, 3352, 1744, 1653, 1377, 1312, 1192, 1119, 1057, 1005, 955, 841, 800, 764

NMR(DMSO-d$_6$)δ: 3.71(3H, s), 5.62(2H, d, J=53 Hz), 7.23(2H, bs), 7.4–8.0(5H, m)

Preparation Example 13

Preparation of O-mesyl-2-methoxycarbonyl-2-fluoromethoxyimino-acetamidoxime of the formula V (wherein $R^1$ is CH$_2$F, $R^2$ is mesyl, and $R^3$ is OMe)

2-Carboxy-2-fluoromethoxyimino-acetamidoxime (3.58 g, 20 mmol) was reacted with methanesulfonyl chloride (2.29 g, 20 mmol) in the same procedure as described in Preparation example 10 to give O-mesyl-2-methoxycarbonyl-2-fluoromethoxyimino-acetamidoxime (2.57 g, yield: 47.4%).

m.p.: 124.5°–127° C.

IR(KBr): 3443, 3337, 1744, 1659, 1441, 1352, 1298, 1177, 1119, 1055, 988, 905, 841, 820

NMR(DMSO-d$_6$)δ: 3.04(3H, s), 3.76(3H, S), 5.74(2H, d, J=53 Hz), 7.20(2H, bs)

Preparation Example 14

Preparation of O-tosyl-2-ethoxycarbonyl-2-methoxyimino-acetamidoxime of the formula V (wherein $R^1$ is Me, $R^2$ is tosyl, and $R^3$ is OEt)

Thionyl chloride (12.5 g, 0.11 mol) was added dropwise to a suspension of 2-carboxy-2-methoxyimino-acetamidoxime (19.8 g containing 19% of sodium chloride, i.e., 16.1 g (0.1 mol) as the substance) in ethanol (30 g). O-Tosyl-2-ethoxycarbonyl-2-methoxyimino-acetamidoxime (25.7 g, yield: 75.0%) was obtained in the same procedure as described in Preparation example 8.

m.p.: 117.5°–119.0° C.

IR(KBr)cm$^{-1}$: 3458, 3356, 1728, 1649, 1599, 1364, 1192, 1042, 837

NMR(CDCl$_3$)δ: 1.23(t, 3H, J=7 Hz), 2.40(s, 3H), 3.98(s, 3H), 4.18(q, 2H, J=7 Hz), 5.35(bs, 2H), 7.20–7.73(m, 4H)

Preparation Example 15

Preparation of 2-cyano-2-fluoromethoxyimino-acetamide of the formula III (wherein $R^1$ is CH$_2$F and $R^3$ is NH$_2$)

Potassium carbonate (85.7 g, 0.62 mol) was added to 2-cyano-2-hydroxyiminoacetamide (35.0 g, 0.31 mol) in dimethylsulfoxide (150 ml) under ice-cooling, and the mixture was stirred for 20 mins. On the other hand, a solution of fluoromethyl bromide (27.8 g, 0.31 mol) in dimethylformamide (27 ml) was added dropwise to the reaction mixture under ice-cooling, and the resultant mixture was stirred at a room temperature for 1.5 hrs. The mixture was dispersed in ice water (1 kg), and it was extracted three times with ethyl acetate (500 ml, 400 ml, and 300 ml, respectively). The combined extracts were washed twice with saturated brine (150 ml) and dried over magnesium sulfate (100 g). The ethyl acetate was distilled off under reduced pressure until the residue weighed 65.5 g. The residue was cooled, filtered, and dried to give 2-cyano-2-fluoromethoxyimino-acetamide (32.8 g, yield: 72.6%).

NMR(DMSO-d$_6$)δ: 5.91(2H, d, J=53 Hz), 7.93(2H, bs)

Preparation Example 16

Preparation of O-tosyl-2-carbamoyl-2-methoxyimino-acetamidoxime of the formula V (wherein $R^1$ is Me, $R^2$ is tosyl, and $R^3$ is NH$_2$)

Sodium carbonate (5.56 g, 0.0525 mol) was added to 2-cyano-2-methoxyimino-acetamide (12.7 g, 0.1 mol) and hydroxylamine hydrochloride (7.3 g, 0.105 mol) in methanol (80 ml), and the mixture was stirred at a room temperature for 17 hrs. and ice-cooled. Sodium carbonate (6.89 g, 0.065 mol) and methanol (20 ml) were added thereto followed by addition of p-toluenesulfonyl chloride (21.0 g, 0.11 mol) in small portions under ice-cooling. The mixture was stirred at the same temperature for 4 hrs, dispersed into water (100 ml) and cooled to separate crystals which were filtered off and washed with water followed by ethyl acetate (80 ml). The crystals were filtered off and dried to give O-tosyl-2-carbamoyl-2-methoxyimino-acetamidoxime (20.2 g, yield: 64.3%).

m.p.: 124°–126° C. (decomp.)

IR(KBr)cm$^{-1}$: 3402, 3196, 1693, 1653, 1597, 1346, 1175, 1047, 895, 831, 667

NMR(DMSO-d$_6$)δ: 2.34(3H, s), 3.74(3H, s), 6.80(2H, bs), 7.11(2H, bs), 7.17(2H, d, J=8 Hz), 7.57(2H, J=8 Hz)

Preparation Example 17

Preparation of O-tosyl-2-carbamoyl-2-fluoromethoxy-acetamidoxime of the formula V (wherein R$^1$ is CH$_2$F, R$^2$ is tosyl, and R$^3$ is NH$_2$)

O-Tosyl-2-carbamoyl-2-fluoromethoxy-acetamidoxime (4.90 g, yield: 73.8%) was obtained in the same procedure as described in Preparation example 16, using 2-cyano-2-fluoromethoxyimino-acetamide (2.90 g, 20 mmol).

m.p.: 143°–145° C. (decomp.)

IR(KBr)cm$^{-1}$: 3421, 1699, 1651, 1599, 1854, 1177, 1059, 1009, 899, 847, 816, 669

NMR(DMSO-d$_6$)δ: 2.37(3H, s), 5.53(2H, d, J=53 Hz), 7.04(2H, bs), 7.23(2H, d, J=8 Hz), 7.43(2H, bs), 7.64(2H, d, J=8 Hz)

Preparation Example 18

Preparation of 2-cyano-2-ethoxyimino-acetamide of the formula III (wherein R$^1$ is Et and R$^3$ is NH$_2$)

62.5% sulfuric acid (69.5 g, 0.44 mol) was added dropwise to a suspension of 2-cyanoacetamide (84 g, 1 mol) and sodium nitrite (82.8 g, 1.2 mol) in water (130 ml), at 35° to 40° C., and the mixture was allowed to react for 3.5 hrs. Potassium carbonate (73.3 g, 0.52 mol) in water (91 ml) was added thereto and then diethyl sulfate (16.9 g, 1.1 mmol) was added dropwise at 35° to 40° C. After completion of the addition, the reaction mixture was stirred at the same temperature for 2 hrs. and cooled to 5° C. The precipitate were filtered off, washed with water and dried to give 2-cyano-2-ethoxyimino-acetamide (130 g, yield: 92.2%).

m.p.: 125.5°–127.0° C.

IR(KBr)cm$^{-1}$: 3417.6, 3182.3, 1712.7, 1610.5, 1487.0, 1386.7, 1190.0, 1049.2, 688.5

NMR(DMSO-d$_6$)δ: 1.35(3H, t, J=7 Hz), 4.46(2H, q, J=7 Hz), 8.23–7.53(2H, bs)

Preparation Example 19

Preparation of 2-carboxy-2-ethoxyimino-acetamidoxime of the formula IV (wherein R$^1$ is Et)

To a suspension of 2-cyano-2-ethoxyimino-acetamide (112.8 g, 0.8 mol) and sodium bicarbonate (134.4 g, 1.6 mol) in water (258 mol), hydroxylamine hydrochloride (61.6 g, 0.88 mol) in water (86 ml) was added dropwise at 80° to 85° C. The mixture was stirred at the same temperature for 3 hrs., and then treated in the same procedure as described in Preparation example 5 to give 2-carboxy-2-ethoxyimino-acetamidoxime (122.5 g) as crystals containing 28.6% of brine. Practical yield: 122.5×0.286=87.5 g. Yield: 62.5%.

m.p.: 140°–141° C. (decomp.)

IR(KBr)cm$^{-1}$: 3338.6, 2937.4, 1693.4, 1604.7, 1485.1, 1473.5, 1365.5, 1103.2, 1041.5, 823.5

NMR(DMSO-d$_6$)δ: 1.25(3H, t, J=7 Hz), 4.18(2H, q, J=7 Hz), 5.77–4.87(2H, bs), 7.60–8.25(1H, bs), 10.03–10.57 (1H, bs)

Preparation Example 20

Preparation of O-tosyl-2-methoxycarbonyl-2-ethoxyimino-acetamidoxime of the formula V (wherein R$^1$ is Et, R$^2$ is tosyl, and R$^3$ is OMe)

Thionyl chloride (58.9 g, 0.495 mol) was added dropwise to a suspension of 2-carboxy-2-ethoxyimino-acetamidoxime (110.4 g including 31.6 g of sodium chloride, i.e., 78.8 g as the substance (0.45 mol)) in methanol (182 ml) under reflux with heating. After completion of the addition, the reaction mixture was heated under reflux for 2 hrs. and then, concentrated under reduced pressure. To the residual liquid, methanol (400 ml), water (300 ml), sodium hydrogencarbonate (113.4 g) and tosyl chloride (90.0 g, 0.47 mol) were added. The mixture was treated in the same procedure as described in Preparation example 8 to give O-tosyl-2-methoxycarbonyl-2-ethoxyimino-acetamidoxime (73.0 g, yield: 47.3%).

m.p.: 111°–121° C. (decomp.)

IR(KBr)cm$^{-1}$: 3444.6, 3354, 1782, 1649, 1440.7, 1357.8, 1305.7, 1180.4, 1029.9, 823.5

NMR(CDCl$_3$)δ: 1.25(3H, t, J=7 Hz), 2.42(3H, a), 3.73 (3H, s), 4.26(2H, q, J=7 Hz), 5.33(2H, bs), 7.24–7.76(4H, m)

Examples

Example 1

Methyl 2-methoxyimino-2-(5-amino-1,2,4-thiadiazole-3-yl)-acetate (anti-isomer) of the formula VI (wherein R$^1$ is Me and R$^3$ is Ome)

O-Tosyl-2-methoxycarbonyl-2-methoxyimino-acetamidoxime (91.6 g, 0.28 mol) was added to potassium rhodanide (81 g, is 0.83 mol) and methanol (265 g) to react at 25° to 30° C. for 24 hrs. The insoluble substance was filtered off and washed with methanol (230 g). The washing methanol solutions were combined with the reaction filtrate, and methanol was distilled off under reduced pressure. To the resultant residue, water (140 g) was added for cooling to form crystals. The formed crystals were filtered off and dried to give methyl 2-methoxyimino-2-(5-amino-1,2,4-thiadiazole-3-yl)-acetate (anti-isomer) (49.3 g, yield: 82.0%).

m.p.: 172°–174° C.

IR(KBr)cm$^{-1}$: 3371, 3124, 1732, 1645, 1531, 1479, 1348, 1294, 1122, 1041, 949

NMR(DMSO-d$_6$)δ: 3.77(s, 3H), 3.92(s, 3H), 8.10(bs, 2H)

Example 2

Methyl 2-methoxyimino-2-(5-amino-1,2,4-thiadiazole-3-yl)-acetate (anti-isomer) of the formula VI (wherein R$^1$ is Me and R$^3$ is OMe)

Methyl 2-Methoxyimino-2-(5-amino-1,2,4-thiadiazole-3-yl)-acetate (5.4 g, yield: 50%) was obtained in the same procedure as described in Example 1, using O-tosyl-2-methoxycarbonyl-2-methoxyimino-acetamidoxime (16.45 g, 0.05 mol) and sodium rhodanide (12.15 g, 0.15 mol).

Example 3

Methyl 2-methoxyimino-2-(5-amino-1,2,4-thiadiazole-3-yl)-acetate (anti-isomer) of the formula VI (wherein $R^1$ is Me and $R^3$ is OMe)

Methyl 2-Methoxyimino-2-(5-amino-1,2,4-thiadiazole-3-yl)-acetate (anti-isomer) (10.1 g, yield; 78.1%) was obtained in the same procedure as described in Example 1, using O-benzenesulfonyl-2-methoxycarbonyl-2-methoxyimino-acetamidoxime (18.9 g, 0.06 mol).

Example 4

Methyl 2-methoxyimino-2-(5-amino-1,2,4-thiadiazole-3-yl)-acetate (anti-isomer) of the formula VI (wherein $R^1$ is Me and $R^3$ is OMe)

methyl 2-methoxyimino-2-(5-amino-1,2,4-thiadiazole-3-yl)-acetate (anti-isomer) (0.47 g, yield: 72.5%) was obtained in the same procedure as described in Example 1, using O-methanesulfonyl-2-methoxycarbonyl-2-methoxyimino-acetamidoxime (0.76 g, 3.0 mmol).

Example 5

Methyl 2-fluoromethoxyimino-2-(5-amino-1,2,4-thiadiazole-3-yl)-acetate (anti-isomer) of the formula VI (wherein $R^1$ is $CH_2F$ and $R^3$ is OMe)

Methyl 2-fluromethoxyimino-2-(5-amino-1,2,4-thiadiazole-3-yl)-acetate (anti-isomer) (902 mg, yield: 59.2%) was obtained in the same procedure as described in Example 1, using O-tosyl-2-methoxycarbonyl-2-fluoromethoxyimino-acetamidoxime (2.26 g, 6.5 mmol).

m.p.: 166°–169° C.

IR(KBr)cm$^{-1}$: 3398, 3138, 1740, 1636, 1529, 1470, 1439, 1375, 1292, 1130, 1088, 1059, 941, 818

NMR(DMSO-d$_6$)δ: 3.72(3H, s), 5.65(2H, d, J=53 Hz), 7.93(2H, s)

Example 6

Methyl 2-fluoromethoxyimino-2-(5-amino-1,2,4-thiadiazole-3-yl)-acetate (anti-isomer) of the formula VI (wherein $R^1$ is $CH_2F$ and $R^3$ is OMe)

Methyl 2-fluoromethoxyimino-2-(5-amino-1,2,4-thiadiazole-3-yl)-acetate (anti-isomer) (835 mg, yield: 35.7%) was obtained in the same procedure as described in Example 1, using O-benzenesulfonyl-2-methoxycarbonyl-2-fluoromethoxyimino-acetamidoxime (3.3 g, 10 mmol).

Example 7

Methyl 2-methoxyimino-2-(5-amino-1,2,4-thiadiazole-3-yl)-acetate (anti-isomer) of the formula VI (wherein $R^1$ is Me and $R^3$ is OEt)

Methyl 2-methoxyimino-2-(5-amino-1,2,4-thiadiazole-3-yl)-acetate (anti-isomer) (2.97 g, yield: 71%) was obtained in the same procedure as described in Example 1, using O-tosyl-2-ethoxycarbonyl-2-methoxyimino-acetamidoxime (5 g, 14.5 mmol).

m.p.: 138°–144° C.

IR(KBr)m$^{-1}$: 3387, 3150, 1734, 1632, 1528, 1271, 1138, 957

NMR(DMSO-d$_6$)δ: 1.28(t, 3H, J=7 Hz), 3.97(s, 3H), 4.22(t, 2H, J=7 Hz), 7.58(bs, 2H)

Example 8

Methyl 2-methoxyimino-2-(5-formamido-1,2,4-thiadiazole-3-yl)-acetate (syn-isomer) of the formula VII (wherein $R^1$ is Me and $R^3$ is OMe):

Methyl 2-methoxyimino-2-(5-amino-1,2,4-thiadiazole-3-yl)-acetate (anti-isomer) (10 g, 0.046 mol) in 99% formic acid (50 g) was heated under stirring at 70° C. for 6 hrs. It was cooled to below 10° C. to separate crystals, which were collected by filtration, washed with methanol and dried to give methyl 2-methoxyimino-2-(5-formamido-1,2,4-thiadiazole-3-yl)-acetate (syn-isomer) (7.6 g, yield: 85%).

m.p.: 238°–240° C.

IR(KBr)cm$^{-1}$: 3230, 3153, 3049, 1745, 1684, 1550, 1541, 1458, 1435, 1369, 1295.9, 1105, 1037, 947

NMR(DMSO-d$_6$)δ: 3.80(3H, s), 3.95(3H, s), 8.85(1H, s), 11.58(1H, bs)

Example 9

Methyl 2-fluoromethoxyimino-2-(5-formamido-1,2,4-thiadiazole-3-yl)-acetate (syn-isomer) of the formula VII (wherein $R^1$ is $CH_2F$ and $R^3$ is OMe)

A solution of methyl 2-fluoromethoxyimino-2-(5-amino-1,2,4-thiadiazole-3-yl)-acetate (anti-isomer) (1.17 g, 5 mmol) in 99% formic acid (2.34 g, 51 mmol) was reacted at 35° C. for 90 hrs. The reaction mixture was cooled to below 10° C. to separate crystals, which were collected by filtration, washed with methanol and dried to give methyl 2-fluoromethoxyimino-2-(5-formamido-1,2,4-thiadiazole-3-yl)-acetate (syn-isomer) (434 mg). The crystals thereof (100 mg) were further obtained from the mother liquor. (Yield: 39.6%).

m.p.: 210°–212° C. (decomp.)

IR(KBr)cm$^{-1}$: 3167, 3055, 2968, 1747, 1684, 1553, 1541, 1439, 1396, 1373, 1283, 1111, 1065, 1009, 968, 932, 862, 787, 735, 575

NMR(DMSO-d$_6$)δ: 3.88(3H, s), 5.80(2H, d, J=54 Hz), 8.73(1H, s), 13.54(1H, bs)

Example 10

Methyl 2-fluoromethoxyimino-2-(5-formamido-1,2,4-thiadiazole-3-yl)-acetate (syn-isomer) of the formula VII (wherein $R^1$ is $CH_2F$ and $R^3$ is OMe)

To a suspension of methyl 2-fluoromethoxyimino-2-(5-amino-1,2,4-thiadiazole-3-yl)-acetate (anti-isomer) (1.17 g, 5 mmol) in formic acid (1.38 g, 30 mmol), acetic anhydride (1.12 g, 10 mmol) was added. The mixture was treated in the same procedure as described in Example 9 to give methyl 2-fluoromethoxyimino-2-(5-formamido-1,2,4-thiadiazole-3-yl)-acetate (syn-isomer) (991 mg, yield: 73.8%).

Example 11

2-methoxyimino-2-(5-amino-1,2,4-thiadiazole-3-yl) acetic acid (syn-isomer) of the formula I (wherein $R^1$ is Me)

To a suspension of methyl 2-methoxyimino-2-(5-formamido-1,2,4-thiadiazole-3-yl)-acetate (syn-isomer) (146 g, 0.60 mmol) in water (720 g) was cooled to an internal temperature of 0° C. and then 10% aqueous sodium hydroxide solution (720 ml) was added dropwise thereto. The mixture was allowed to react at a temperature in the range of 0°±1° C. for 1 hr., then heated to an internal temperature of 45° to 50° C. to react for 2 hrs. The reaction mixture was then neutralized with concentrated hydrochloric acid (62.4 g) to pH 6.5 to 7.5., and concentrated at an internal temperature of below 60° C. and then adjusted to pH 3 with concentrated hydrochloric acid (62 g). After that, it was decolorized and purified with activated carbon (14.6 g), followed by the addition of concentrated hydrochloric acid (62.4 g). It was then cooled to separate crystals which were collected by filtration and dried to give 2-methoxyimino-2-(5-amino-1,2,4-thiadiazole-3-yl) acetic acid (syn-isomer) (166.7 g, yield: 88.0%, and purity by HPLC: 99.4%).

m.p.: 170°–171° C. (decomp.)

IR(KBr)cm$^{-1}$: 3447, 3173, 1726, 1620, 1539, 1491, 1244, 1155, 1043, 829

NMR(DMSO-d$_6$)δ: 3.92(s, 3H), 7.92(bs, 2H)

Example 12

2-fluoromethoxyimino-2-(5-amino-1,2,4-thiadiazole-3-yl) acetic acid (syn-isomer) of the formula I (wherein R$^1$ is CH$_2$F)

To a suspension of methyl 2-fluoromethoxyimino-2-(5-formamido-1,2,4-thiadiazole-3-yl)-acetate (syn-isomer) (5.24 g, 20 mmol) in water (26 ml), sodium hydroxide (3.2 g, 80 mmol) in water (16 ml) was added at 0° C., and the mixture was stirred at 5° C. for 30 hrs. and then adjusted to pH 1 or lower with concentrated hydrochloric acid (7.0 ml, 84 mmol), and extracted four times with ethyl acetate (30 ml). The resulting ethyl acetate layer was dried over sodium sulfate and decolorized with activated carbon (0.5 g). The ethyl acetate was distilled off, to the residue, isopropyl ether was added. The resultant solution was cooled to precipitate. The precipitates were filtered off and dried to give 2-fluoromethoxyimino-2-(5-amino-1,2,4-thiadiazole-3-yl) acetic acid (syn-isomer) (36 g, yield: 81.8%).

m.p.: 169°–172° C. (decomp.)

IR(KBr)cm$^{-1}$: 1736, 1620, 1537, 1423, 1248, 1175, 1146, 1082, 1011, 957, 824, 721

NMR(DMSO-d$_6$)δ: 5.78(2H, d, J=55 Hz), 8.15(3H, bs)

Example 13

2-fluoromethoxyimino-2-(5-amino-1,2,4-thiadiazole-3-yl) acetamide (anti-isomer) of the formula VI (wherein R$^1$ is CH$_2$F and R$^3$ is NH$_2$)

O-tosyl-2-carbamoyl-2-fluoromethoxyimino-acetamidoxime (3.32 g, 10 mmol) was added to potassium rhodanide (2.92 g, 30 mmol) and methanol (12 ml), and the mixture was stirred at a room temperature for 24 hrs. The insoluble substance was collected by filtration and washed with methanol (12 ml). The washing filtrates were combined with the reaction filtrate, and the methanol was distilled off under reduced pressure. The residue was dispersed in water (15 ml), and the resultant solution was cooled to precipitate. The precipitates were collected by filtration and dried to give 2-fluoromethoxyimino-2-(5-amino-1,2,4-thiadiazole-3-yl) acetamide (anti-isomer) (1.64 g, yield: 74.9%).

m.p.: 182°–184° C. (decomp.)

IR(KBr)cm$^{-1}$: 3342, 3167, 1692, 1638, 1539, 1441, 1402, 1356, 1144, 1088, 1049, 984, 943, 918, 567

NMR(DMSO-d$_6$)δ: 5.69(2H, d, J=54 Hz), 7.53(1H, bs), 7.68(1H, bs), 7.93(2H, s)

Example 14

2-methoxyimino-2-(5-amino-1,2,4-thiadiazole-3-yl) acetamide (anti-isomer) of the formula VI (wherein R$^1$ is Me and R$^3$ is NH$_2$)

O-Tosyl-2-carbamoyl-2-methoxyiminoacetamidoxime (8.80 g, 28 mmol) was added to potassium rhodanide (8.16 g, 84 mmol) and methanol (35 ml), and the mixture was stirred at a room temperature for 24 hrs. The insoluble substance was collected by filtration and washed with methanol (35 ml). The washing filtrates were combined with the reaction filtrate, and the methanol was distilled off under reduced pressure. The residue was purified by silica gel chromatography (chloroform:methanol=7:1) to give 2-methoxyimino-2-(5-amino-1,2,4-thiadiazole-3-yl) acetamide (anti-isomer) (3.80 g, yield: 67.5%)

m.p.: 165°–168° C. (decomp.)

IR(KBr)cm$^{-1}$: 3329, 1682, 1630, 1529, 1356, 1150, 1042, 949

NMR(DMSO-d$_6$)δ: 3.85(3H, s), 7.30(1H, bs), 7.37(1H, bs), 7.81(2H, bs)

Example 15

2-fluoromethoxyimino-2-(5-formamido-1,2,4-thiadiazole-3-yl) acetamide (syn-isomer) of the formula VII (wherein R$^1$ is CH$_2$F and R$^3$ is NH$_2$)

To a suspension of 2-fluoromethoxyimino-2-(5-amino-1,2,4-thiadiazole-3-yl) acetamide (anti-isomer) (3.51 g, 16 mmol) in 99% formic acid (14.73 g, 320 mmol), acetic anhydride (4.90 g, 48 mmol) was added, and the mixture was reacted at 40° C. for 50 hrs, and then cooled to below 10° C. to separate crystals. The crystals were collected by filtration and washed with cold methanol (10 ml) on Nutsche. The crystals in DMF (16 ml) were heated to dissolve and the resulting solution was dispersed in methanol (32 ml), and then cooled, filtered and dried to give 2-fluoromethoxyimino-2-(5-formamido-1,2,4-thiadiazole-3-yl) acetamide (syn-isomer) (2.43 g, yield: 61.4%). The content obtained by HPLC: 99.0% (anti-isomer: 0.2%).

m.p.: 243°–246° C. (decomp.)

IR(KBr)cm$^{-1}$: 3373, 3198, 1703, 1666, 1611, 1549, 1281, 1072, 1013, 957, 870

NMR(DMSO-d$_6$)δ: 5.76(2H, d, J=55 HZ), 7.76(1H, bs), 8.03(1H, bs), 8.71(1H, s), 13.46(1H, bs)

Example 16

2-methoxyimino-2-(5-formamido-1,2,4-thiadiazole-3-yl) acetamide (syn-isomer) of the formula VIII (wherein R$^1$ is Me and R$^3$ is NH$_2$)

2-Methoxyimino-2-(5-amino-1,2,4-thiadiazole-3-yl) acetamide (anti-isomer) (604 mg, 3 mmol) obtained in Example 14 was dissolved in 99% formic acid (3.45 g, 75 mmol), and the solution was heated under stirring at 70° C. for 7 hrs. The reaction mixture was treated in the same procedure as in Example 8 to give 2-methoxyimino-2-(5-formamido-1,2,4-thiadiazole-3-yl) acetamide (syn-isomer) (489 mg, yield: 71.1%).

m.p.: 269°–271° C. (decomp.)

IR(KBr)cm$^{-1}$: 3360, 3197, 1703, 1663, 1611, 1549, 1404, 1281, 1109, 1047, 874

NMR(DMSO-d$_6$)δ: 3.87(3H, S), 7.50(1H, b.s), 7.76(1H, bs), 8.59(1H, s), 13.44(1H, b.s)

Example 17

2-methoxyimino-2-(5-formamido-1,2,4-thiadiazole-3-yl) acetamide (syn-isomer) of the formula VII (wherein R$^1$ is Me and R$^3$ is NH$_2$)

Potassium rhodanide (5.83 g, 60 mmol), methanol (24 ml) and O-tosyl-2-carbamoyl-2-methoxyiminoacetamidoxime (6.29 g, 20 mmol) were treated in the same procedure as in Example 14, so that a residue (9.21 g) from which methanol was thoroughly distilled off was obtained. Then 99% formic acid (27.6 g, 600 mmol) was added to the obtained residue without purification. The mixture was stirred at 70° C. for 4 hrs. and cooled. Acetic anhydride (8.97 g, 80 mmol) was added thereto, and the resultant mixture was stirred at 35° C. for 48 hrs. and then dispersed in methanol (40 ml) and cooled to below 10° C. It was filtered and dried to give 2-methoxyimino-2-(5-formamido-1,2,4-thiadiazole-3-yl) acetamide (syn-isomer) (1.93 g, yield: 42.5%).

Example 18

Methyl 2-ethoxyimino-2-(5-amino-1,2,4-thiadiazole-3-yl)-acetate (anti-isomer) of the formula VI (wherein $R^1$ is Et and R is OMe)

Methyl 2-Ethoxyimino-2-(5-amino-1,2,4-thiadiazole-3-yl)-acetate (anti-isomer) (12.5 g, yield: 67.9%) was obtained in the same procedure as in Example 1, using O-tosyl-2-methoxycarbonyl-2-ethoxyiminoacetamidoxime (27.4 g, 0.08 mol)

m.p.: 183°–193° C. (decomp.)

IR(KBr)cm$^{-1}$: 3386.8, 3134.1, 1730, 1627.8, 1523.7, 1479.3, 1365.5, 1288.4, 1137.9, 1039.6, 956.6, 813.9

NMR(DMSO-$d_6$)δ: 1.22(3H, t, J=7 Hz), 3.33(3H, s), 4.29(2H, q, J=7 Hz), 8.09(2H, bs)

Example 19

Methyl 2-ethoxyimino-2-(5-formamido-1,2,4-thiadiazole-3-yl)-acetate (syn-isomer) of the formula VII (wherein $R^1$ is Et and $R^3$ is OMe)

Methyl 2-ethoxyimino-2-(5-amino-1,2,4-thiadiazole-3-yl)-acetate (anti-isomer) (5.75 g, 25 mmol) in 99% formic acid (16.3 g) was heated under stirring at 75° C. for 6 hrs. The reaction mixture was treated in the same procedure as in Example 8 to give methyl 2-ethoxyimino-2-(5-formamido-1,2,4-thiadiazole-3-yl)-acetate (syn-isomer) (3.2 g, yield: 49.6%).

m.p.: 204°–207° C. (decomp.)

IR(KBr)cm$^{-1}$: 3159.2, 2958.6, 1745.5, 1683.7, 1539.1, 1369.4, 1103.2, 1039.6, 952.8, 867.9,

NMR(DMSO-$d_6$)δ: 1.29(3H, t, J=7 Hz), 3.90(3H, s), 8.90(s, 1H), 12.16(1H, bs)

Example 20

2-Ethoxyimino-2-(5-amino-1,2,4-thiadiazole-3-yl) acetic acid (syn-isomer) of the formula I (wherein $R^1$ is Et)

2-Ethoxyimino-2-(5-amino-1,2,4-thiadiazole-3-yl) acetic acid (syn-isomer) (1.46 g, yield: 84.5%) was obtained in the same procedure as in Example 11, using methyl 2-ethoxyimino-2-(5-formamido-1,2,4-thiadiazole-3-yl)-acetate (syn-isomer) (2.06 g, 8 mmol).

m.p.: 170.5°–172.0° C. (decomp.)

IR(KBr)cm$^{-1}$: 3435, 3165, 2983.7, 1683.7, 1614, 1537.2, 1460, 1411.8, 1355.9, 1166.9, 1039.6, 1010.6, 927.7, 831.3

NMR(DMSO-$d_6$)δ: 1.33(3H, t, J=7 Hz), 4.25(2H, q, J=7 Hz), 8.25(2H, bs)

What is claimed is:

1. A method of preparing 2-substituted hydroxyimino-2-(5-amino-1,2,4-thiadiazol-3-yl)acetic acid derivatives (anti-isomer) of the general formula (VI):

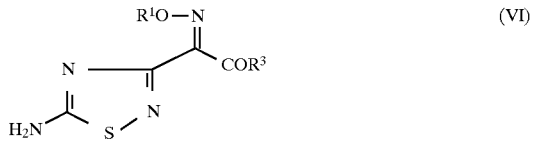

wherein $R^1$ is lower alkyl or fluoromethyl, $R^3$ is lower alkyloxy or amino, which comprises reacting of 2-substituted hydroxy-imino-2-substituted carbonyl-acetamide-O-substituted oxime (V) of the general formula (V):

wherein $R^1$ and $R^3$ have the same meanings as above and $R^2$ is alkylsulfonyl or arylsulfonyl, with MSCN wherein M is alkaline metal or ammonium.

2. A method of preparing 2-substituted hydroxyimino-2-(5-formamido-1,2,4-thiadiazol-3-yl)acetic acid derivatives (syn-isomer) of the general formula (VII):

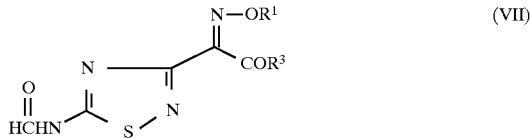

wherein $R^1$ is lower alkyl or fluoromethyl, $R^3$ is lower alkyloxy or amino, which comprises reacting of formic acid with 2-substituted hydroxyimino-2-(5-amino-1,2,4-thiadiazol-3-yl)acetic acid derivatives (anti-isomer) of the general formula (VI):

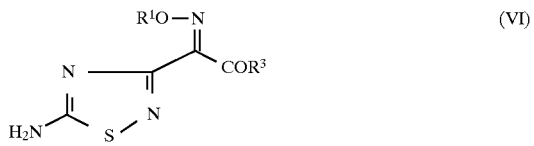

wherein $R^1$ and $R^3$ have the same meanings as above.

3. The method of claim 2 wherein formic acid is used in an amount of 2 to 10 times by weight based on the weight of the compound of formula (VI), and compound of formula (VII) is precipitated as the reaction proceeds.

4. The method of claim 2 wherein compound of formula (VII) is recovered by steps comprising cooling the reaction mixture to separate crystals comprising compound of formula (VII).

* * * * *